United States Patent
Vivier et al.

(10) Patent No.: US 7,342,045 B2
(45) Date of Patent: Mar. 11, 2008

(54) STABILIZED ASCORBIC ACID SOLUTIONS; USE THEREOF; PROCESS FOR THEIR OBTENTION; AND FORMULATIONS COMPRISING THE SAME

(76) Inventors: Ghislain Vivier, 2689 Carriage Way, St-Lazare, Quebec (CA) J7T 2B1; Anthony Costa, 2229 rue de Ronda, Vimont, Quebec (CA) H7K 3T4

( * ) Notice: Subject to any disclaimer, the term of this patent is extended or adjusted under 35 U.S.C. 154(b) by 435 days.

(21) Appl. No.: 10/363,929

(22) Filed: Mar. 7, 2003

(65) Prior Publication Data

US 2006/0029687 A1 Feb. 9, 2006

Related U.S. Application Data

(63) Continuation-in-part of application No. PCT/CA01/01270, filed on Sep. 10, 2001.

(60) Provisional application No. 60/231,068, filed on Sep. 8, 2000.

(51) Int. Cl.
*A61K 31/375* (2006.01)

(52) U.S. Cl. .................. 514/474; 424/401; 424/736

(58) Field of Classification Search .................. None
See application file for complete search history.

(56) References Cited

U.S. PATENT DOCUMENTS

| | | | |
|---|---|---|---|
| 4,983,382 A | 1/1991 | Wilmott et al. | |
| 5,093,360 A * | 3/1992 | Yu et al. ..................... | 514/463 |
| 5,140,043 A | 8/1992 | Darr et al. | |
| 5,736,567 A | 4/1998 | Cantin et al. | |
| 5,827,520 A * | 10/1998 | de Salvert .................. | 424/401 |
| 5,869,063 A | 2/1999 | Lezdey et al. | |
| 5,935,584 A | 8/1999 | Guerrero et al. | |
| 5,972,360 A | 10/1999 | Braun | |
| 6,087,393 A | 7/2000 | Mathur | |
| 6,103,267 A | 8/2000 | Mitchnick et al. | |
| 6,124,348 A | 9/2000 | Wells et al. | |
| 6,284,234 B1 * | 9/2001 | Niemiec et al. ......... | 424/78.07 |

FOREIGN PATENT DOCUMENTS

| | | |
|---|---|---|
| DE | 100 09 252 | 9/2001 |
| EP | 0 884 045 | 12/1998 |
| WO | 98/23152 | 6/1998 |

OTHER PUBLICATIONS

Database Embase Online!; Elsevier Science Publishers, Amsterdam, NL; retrieved from STN Database accession No. 77048093; XP002198232, 1976.

* cited by examiner

*Primary Examiner*—Susan Coe Hoffman

(57) ABSTRACT

This invention relates to improved solutions comprising ascorbic acid (vitamin C). These solutions may comprise as much as 15% ascorbic acid; they are stable for at least two years, without no significant development of yellowish coloration and no substantial (not more than 10%) degradation of the vitamin. The process involves sequential additions of ascorbic acid and ethoxydiglycol to a first solution of vitamin in water, which are followed by addition of propylene glycol. The high stirring speed that occurs during the additions favorises a process of micronisation. Mild heating is used to achieve ascorbic acid concentrations equivalent to about 6% in 10% water or higher.

31 Claims, 2 Drawing Sheets

STABILIZED ASCORBIC ACID SOLUTIONS; USE THEREOF; PROCESS FOR THEIR OBTENTION; AND FORMULATIONS COMPRISING THE SAME

CROSS REFERENCE TO RELATED APPLICATIONS

This Application is a Continuation-In-Part of PCT Patent Application PCT/CA01/01270, filed on Sep. 10, 2001, which claims priority of U.S. provisional patent application 60/231,068, filed on Sep. 8, 2000.

FIELD OF THE INVENTION

The present invention relates to stabilized ascorbic acid solutions, use thereof, process for their obtention, and formulations comprising the same. This invention further relates to a process for the obtention of such stabilized ascorbic acid solutions.

BACKGROUND OF THE INVENTION

Skin appearance and elasticity has always been a cosmetic concern for almost everybody. Skin protection against actinic radiations has become a great health concern over the past ten to twenty years. UV exposure results in the formation of noxious reactive oxygen species (ROS). Skin damages cannot only be life threatening, but they contribute for premature skin ageing. The most popular way by which UV damages are prevented is to block their penetration through the skin using sunscreen formulations. The notion that antioxidants may also be used to improve the therapeutic or cosmetic performance of dermatological formulations is more recent. Antioxidants would in that case have a role in neutralizing ROS or preventing their formation into the skin. Antioxidants include compounds such as ascorbic acid and complexes, tocopherol, tocopheryl acetate, retinol, retinyl palmitate, hydroquinone, proanthocyaniadins, butylated hydroxytoluene, butylated hydroxyanisole, astaxanthin, alpha lipoic acid, tocotrienols, certain proteins and coenzyme Qio. Each antioxidant may be used alone or in combination with each another as active ingredients or as stabilizing and preservation agents to protect other active ingredients against oxidative damages. Antioxidants may also be used alone or in combination with reducing agents such as L-cysteine or glutathione.

Antioxidants need to remain in their unoxidized form in order to be efficacious against ROS. Maintenance of antioxidants stability in solutions has been a challenge over the past years.

Ascorbic acid, also known as vitamin C, is certainly one of the most popular antioxidants. This vitamin is known for its general essential role in maintaining health. In dermatology, vitamin C is known for its implication in collagen synthesis as well as for its antioxidant function, which ultimately helps reduce the expression of skin ageing, translated into the appearance of fine lines or wrinkles in the skin. Vitamin C also has an anti-tyrosinase effect on the skin for skin whitening effect.

Vitamin C is a moderately strong reducing agent, which makes it unstable in aqueous solutions, especially at high pHs. It is particularly subject to oxidative degradation.

Water is one of the best solvents to dissolve ascorbic acid. Its limit of solubility appears to be about 330 mg/ml in water. Ascorbic acid is therefore relatively soluble in water. It is much less soluble in glycols such as propylene glycol (50 mg/ml) and in alcohols such as ethanol (10 mg/ml in absolute ethanol).

Although water is the best solvent to provide an ascorbic acid solution, it is paradoxically one of the worst to protect ascorbic acid against oxidative damages. A proportion of water needs to be replaced with another solvent that provides more stability.

The problem to be solved with ascorbic acid formulations has always been to find a compromise between solubilization and stability.

U.S. Pat. No. 5,140,043 discloses an ascorbic acid formulation that has a pH below 3.5, preferably below 2.5. A low pH insures that a high proportion of ascorbic acid remains in the protonated, uncharged form. The protonated form is more stable and more easily permeant through skin and mucosae membranes than the non-protonated counterpart. Metals also negatively influence the preponderance of the protonated form of ascorbic acid in a solution. A chelator may therefore be added in ascorbic acid solutions to stabilize the vitamin. The carrier in which the ascorbic acid is dissolved comprises an alkylene glycol, namely propylene glycol. The carrier further comprises hydroxyalkylcellulose, the polyhydroxyl function of which apparently participates in the typical reactions of alcohols. The proportion of water remains very high (more than 50% by weight), which may lead to a relatively rapid degradation at room temperature.

U.S. Pat. No. 4,983,382 discloses the use of polyhydric liquids to solubilize and stabilize ascorbic acid. A mixture of ethanol 55-65% and propylene glycol 20-25% is especially preferred for its excellent cosmetic properties. Water may be present in concentrations up to 12% without adversely affecting the stability of ascorbic acid solubilized in a mixture of alcohol and propylene glycol. The organic solvents, all combined, represent up to 90% by weight of a composition. The low water contents recommended does not appear to permit solubilization of more than 10% of ascorbic acid.

U.S. Pat. No. 6,124,348 proposes to combine ascorbic acid, a volatile organic solvent such as isodecane and a gelling base. The solvent does not react with or solubilize the vitamin. Such a suspension is applied to the skin. The skin moisture penetrates the suspension and solubilizes the ascorbic acid which then can permeate the skin layer. The solubility of ascorbic acid in the formulation is not dealt with in this patent.

Another type of dispersion of ascorbic acid is disclosed in U.S. Pat. No. 6,103,267. Again, this patent does not describe a solution of ascorbic acid.

Another approach to stabilize ascorbic acid solution has been to decrease water activity in the same. U.S. Pat. No. 5,736,567 discloses compositions wherein water activity is decreased below 0.85. The lowest water activity achieved with the descriptive examples has been 0.63. At this value, the water content is 21%, the ascorbic acid concentration is 3%, the polypropylene glycol content is 39.4% and polyethylene glycol content is 13% (all percentages given by weight of formulation). The aqueous phase is combined with an oil phase to provide a composition that has a "structure". This particular formulation has been tested for its stability. After two months at 20° C., 0.7% of ascorbic acid has degraded which is fairly good compared to the same solution prepared with 28% water (3.5% degradation) and a composition also comprising 28% water but without the glycols (6.2% degradation). The concentration of ascorbic acid that may be present in these formulations is not higher than 10%.

U.S. Pat. No. 6,087,393 discloses a composition comprising ascorbic acid in a mixed glycerol carrier. The glycerol carrier comprises propylene glycol and butylene glycol, as well as a stabilizer which may be diethylene glycol monoethylether. The preferred proportions of propylene glycol, butylene glycol and diethylene glycol monoethylether are 25-80%, 5-30% and 5-10%, respectively. Ascorbic acid may be present in concentrations comprised between 2% and 15%. In these solutions, the major glycol component is clearly propylene glycol while butylene glycol is added as a solubilizing aid and diethylene glycol monoethylether is added in minor proportion as a stabilizer. The stability of these solutions is not excellent because, at best, the samples admittedly start to develop a yellowish colour after one month at room temperature.

Another approach to formulate and use ascorbic acid in dermatology has been not to deal with its stability. U.S. Pat. No. 5,953,584 proposes to provide separate compartments that are extemporaneously mixed together prior to use. One compartment comprises vitamin C, the other one comprises an aqueous phase. Once reconstituted by admixing the contents of both compartments, ascorbic acid is provided in a solution that is more alkaline than usual solutions of ascorbic acid. The limit of solubility of the vitamin achieved with such a solution is close to 50%. Further, once reconstituted, the ascorbic acid formulation comprises about half-and-half polyethylene glycol and water.

In view of the foregoing, there is still a need to develop a solubilized ascorbic acid in suitable concentrations, and which remains stable for a practical shipping and storage amount of time, and which keeps a clear substantially non-coloured visual aspect for the same amount of time.

SUMMARY OF THE INVENTION

It is a first goal of this invention to provide a solution of ascorbic acid that is stable at least for about twenty-four months. The solution may comprise concentrations of ascorbic acid as high as 5 to 15%.

The solution comprises a carrier essentially formed of water, ethoxydiglycol and propylene glycol. Ethoxydiglycol is the major glycol component. The solution may be used as is or combined to other carriers to provide a plurality of different topical formulations or compositions. Sprays, emulsions, droplets, creams, ointments, milks and lotions are all examples of suitable compositions. The solutions and compositions may be used to prevent or treat a disease or disorder caused by ROS, namely consequent to U.V. or sun exposure. They may further include an anti-oxidant or a reducing agent and they may also include sunblocking ingredients, and depigmentation (skin whitening) agents or other cosmetically valuable compounds. Compositions comprising the present vitamin C solution and one or more of an α-hydroxy acid, retinol, kojic acid, hydroquinone, wine extracts kinetin, vitamin K, ascorbyl palmitate, and magnesium and sodium ascorbyl phosphate are all examples of specific cosmetic compositions which are objects of this invention.

It is another object of this invention to provide a process by which such a stable vitamin C solution can be obtained, which involves sequential additions of vitamin and ethoxydiglycol, followed by propylene glycol, under high stirring speed. If needed, a last addition of ascorbic acid and heating steps are performed to achieve high concentrations of the vitamin. The high stirring speed provides for micronizaton of the components, which is responsible for the stability of the solutions.

As used herein, the terminology "anti-oxidant plant extract" is meant to refer to plant, seed, herb, spice or fruit extract.

BRIEF DESCRIPTION OF THE DRAWINGS

This invention will be described hereinbelow by reference to the following preferred embodiments and appended figures which purpose is to illustrate rather than to limit its scope.

In the appended drawings.

DETAILED DESCRIPTION OF SPECIFIC EMBODIMENTS OF THE INVENTION

Figure 1:
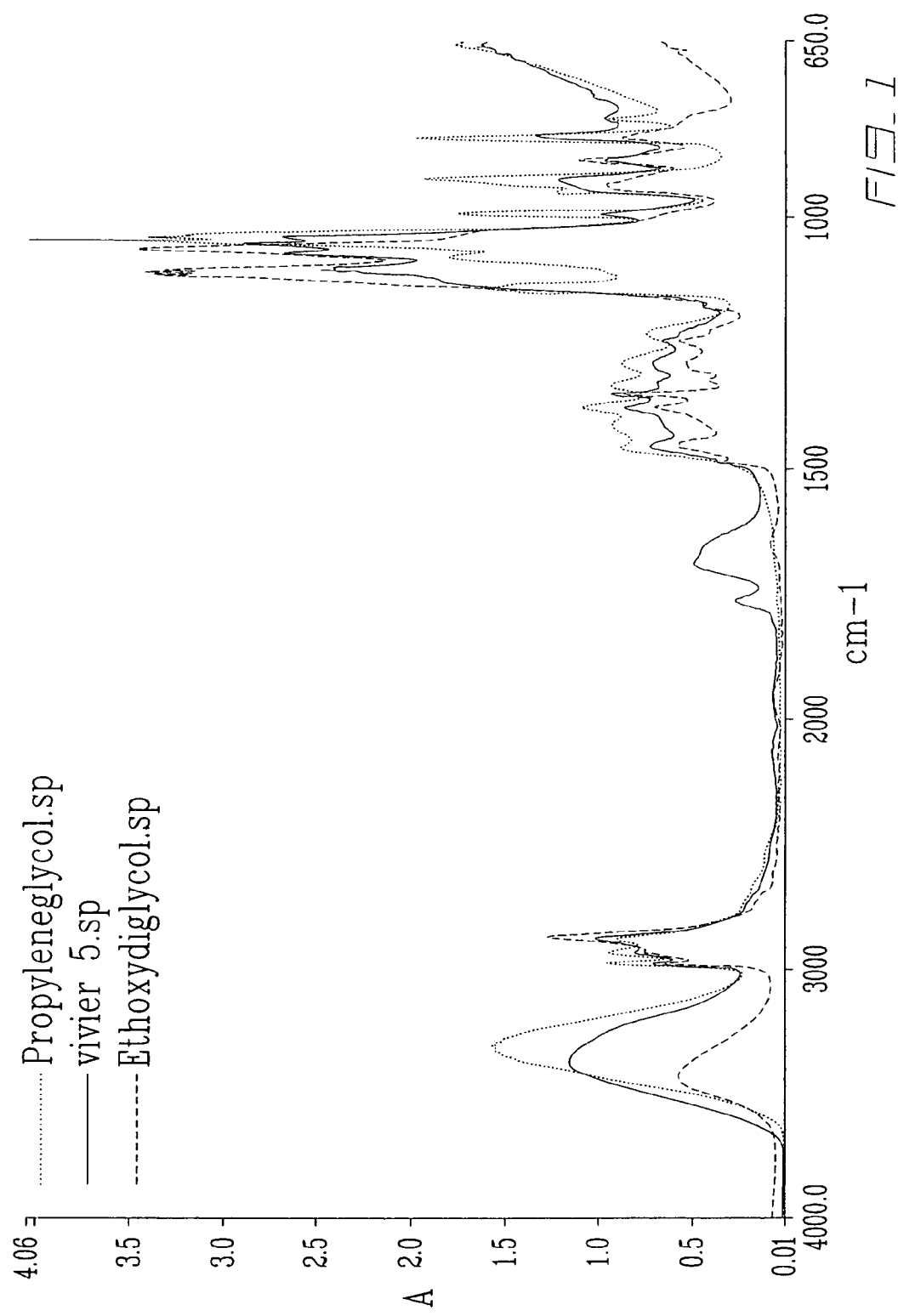
FIG. 1 represents superimposed chromatograms of the present solution (5% ascorbic acid) and of the two glycols composing the carrier.

This process comprises the step of dissolving a first quantity of ascorbic acid in 10% water, which is followed by addition of a first quantity of ethoxydiglycol, under high stirring speed. The step of adding ascorbic acid and ethoxydiglycol can be repeated numerous times (at least one other time), depending on the concentration of ascorbic acid that is sought. After sequential additions of second or third quantities of ascorbic acid and ethoxygylcol, propylene glycol is added to contribute, with water, in the solubilization of ascorbic acid. The rapid agitation and the presence of ethoxydiglycol after each sequential addition of ascorbic acid provide for a micronized and stabilized solution.

When concentrations of ascorbic acid higher than about 6% are needed, a mild heating step (at least about 37-42° C., preferably 40° C.) is required to solubilize the last added quantities of vitamin, in the presence of propylene glycol. For formulating the highest vitamin C concentration of 15%, the concentration of water is increased from 10% to 15%. In such a case, sequential additions of ascorbic acid and ethoxydiglycol may achieve a concentration such that a higher concentration is achieved (12% again in the presence of propylene glycol) prior to heating. A last addition of vitamin can be made, followed by a last heating step. Upon cooling at room temperature, the solution remains stable.

The selection of the right solvents which involves particularly a high concentration of ethoxydiglycol, and of the right sequential additions of ascorbic acid, ethoxydiglycol and propylene glycol, combined to a high speed that allows micronization of ascorbic acid into such a solution, all contribute to obtaining a stable solution of ascorbic acid. Heat contributes to increasing the amount of solubilized ascorbic acid.

A micronization process appears to result in a product wherein the contact of oxygen with the vitamin, is sharply reduced once the latter is in solution. This reduces the oxidative damages to the precious vitamin. The process provides for a solution that has a shelf life of at least about two years, without any substantial development of yellowish colour, which is without any precedent (Data not shown).

Formulations for the Vitamin-C 5%, -10% and 15% according to specific embodiments are as follows:

| Item | Ingredient | 5% % w/w | 10% % w/w | 15% % w/w | 10% % w/w | 10% % w/w | 10% % w/w |
| --- | --- | --- | --- | --- | --- | --- | --- |
| 1. | Demineralized water grade USP | 10.0 | 10.0 | 15.0 | 12.0 | 12.0 | 10.0 |
| 2. | L-Ascorbic Acid grade USP | 5.0 | 10.0 | 15.0 | 10.0 | 10.0 | 10.0 |
| 3. | Ethoxydiglycol grade USP | 54.7 | 51.7 | 46.8 | 48.90 | 46.90 | 51.88 |
| 4. | Anti-oxidant agent | 1.0 | 1.0 | 0.9 | 1.0 | 1.0 | 1.0 |
| 5. | Propylene Glycol grade SUP | 29.0 | 27.0 | 22.0 | 26 | 26.0 | 27.0 |
| 6. | Fragrance material grade MFR | 0.30 | 0.30 | 0.30 | 0.10 | 0.10 | 0.10 |
| 7. | Hydroquinone grade USP | | | | 2.0 | 4.0 | |
| 8. | Kinetin grade MFR | | | | | | 0.03 |

Item 6 appears optional, since it is a fragrance that is added to confer more attractive properties to the solution for the consumer. In specific embodiments presented in the examples below, Apple crunch™ was used as fragrance material because of its availability on the market. Other fragrance may be used such as Apple fresh™. Item 4 is used as an anti-oxidant. Items 7 and 8 are further anti-oxidants used in specific embodiments.

General Manufacturing Procedure

The following sequence has been adopted to prepare a vitamin-C 5% to 15% formulations or compositions. The solution is mixed until clear after every addition. All percentages are given by weight of final composition. All steps, except the heating step, if required, are performed at room temperature (18-25° C.).

EXAMPLE 1

Ascorbic Acid 5% (w/w):
Begin with 10.0% Demineralized water,
add 3.00% L-Ascorbic Acid (Hoffman Laroche) and begin mixing at a medium to high speed (Lightning Mixer or Agitator) add 27.35% Ethoxydiglycol Trivalin SF™,
add 2.00% Vitamin-C (Hoffman Laroche),
add 27.35% Ethoxydiglycol Trivalin SF™,
add 29.00% Propylene Glycol,
add 1.00% Greentech™ Grapefruit Extract, and
add 0.3% Apple Crunch™ Fragrance,
Note: no heating is required.

EXAMPLE 2

Ascorbic Acid 10% (w/w):
Begin with 10.0% Demineralized water,
add 3.00% L-Ascorbic Acid (Hoffman Laroche) and begin mixing at a medium to high speed,
add 25.85% Ethoxydiglycol Trivalin SF™,
add 1.50% Vitamin-C (Hoffman Laroche),
add 25.85% Ethoxydiglycol Trivalin SF™,
add 3.50% Vitamin-C (Hoffman Laroche),
add 27.00% Propylene Glycol, and
add 1.00% Greentech™ Grapefruit Extract.

Heat is then applied in the formulation process. This is an important step in order to formulate a concentration of vitamin-C higher than 6% in the solution comprising 10% water. Interestingly enough, the vitamin-C does not support heat well as the latter tends to oxidize the former. However, the medium in which ascorbic acid is during heating provides protection against oxidative damage.

Therefore, a last addition of 2% Vitamin-C is performed, followed by heating to 40 degrees Celcius until the solution becomes all clear and until all vitamin-C has been dissolved.

While stirring continues, the solution is allowed to cool down at ambient temperature and then, once cooled, 0.3% Apple Crunch™ Fragrance is added.

EXAMPLE 3

Ascorbic Acid 15% (w/w):
Begin with 15.0% Demineralized water,
add 4.5% Vitamin-C (Hoffman Laroche) and being mixing at a medium to high speed,
add 23.4% Ethoxydiglycol,
add 2.25% Vitamin-C (Hoffman Laroche),
add 23.4% Ethoxydiglycol Trivalin SF™,
add 5.25% Vitamin-C (Hoffman Laroche),
add 22.0% Propylene Glycol,
add 0.09% Greentech™ Grapefruit Extract,
and 3.0% Vitamin-C (Hoffman Laroche) and heat solution to 40 degrees Celcius until solution becomes all clear and when all vitamin-C has been dissolved While stirring continues, the solution is cooled down and once cooled, 0.3% Apple Crunch™ Fragrance is added.

EXAMPLE 4

Ascorbic Acid 10% (w/w) and Hydroquinone 2% (w/w):
Begin with 12.0% Demineralized water,
add 3% Vitamin-C (Hoffman Laroche) and being mixing at a medium to high speed,
add 24.45% Ethoxydiglycol,
add 1.5% Vitamin-C (Hoffman Laroche),
add 24.45% Ethoxydiglycol Trivalin SF™,
add 3.5% Vitamin-C (Hoffman Laroche),
add 26.0% Propylene Glycol,
add 1% Greentech™ Grapefruit Extract,
and 2.0% Vitamin-C (Hoffman Laroche) and heat solution to 40 degrees Celcius until solution becomes all clear and when all vitamin-C has been dissolved.

While stirring continues, the solution is cooled down and once cooled, 0.1% Apple Crunch™ Fragrance and 2.0% hydroquinone are added.

EXAMPLE 5

Ascorbic Acid 10% (w/w) and Hydroquinone 4% (w/w):
Begin with 12.0% Demineralized water,
add 3% Vitamin-C (Hoffman Laroche) and being mixing at a medium to high speed, add 23.45% Ethoxydiglycol,
add 1.5% Vitamin-C (Hoffman Laroche),
add 23.45% Ethoxydiglycol Trivalin SF™,
add 3.5% Vitamin-C (Hoffman Laroche),
add 26.0% Propylene Glycol,
add 1% Greentech™ Grapefruit Extract,
and 2.0% Vitamin-C (Hoffman Laroche) and heat solution to 40 degrees Celcius until solution becomes all clear and when all vitamin-C has been dissolved.

While stirring continues, the solution is cooled down and once cooled, 0.1% Apple Crunch™ Fragrance and 4.0% hydroquinone are added.

EXAMPLE 6

Ascorbic acid 10% (w/w) and kinetin:
Begin with 10.0% Demineralized water,
add 3% Vitamin-C (Hoffman Laroche) and being mixing at a medium to high speed,
add 25.935% Ethoxydiglycol,
add 1.5% Vitamin-C (Hoffman Laroche),
add 25.935% Ethoxydiglycol Trivalin SF™,
add 3.5% Vitamin-C (Hoffman Laroche),
add 27.0% Propylene Glycol,
add 1% Greentech™ Grapefruit Extract,
and 2.0% Vitamin-C (Hoffman Laroche) and heat solution to 40 degrees Celsius until solution becomes all clear and when all vitamin-C has been dissolved.

While stirring continues, the solution is cooled down and once cooled, 0.1% Apple Crunch™ Fragrance and 0.03% kinetin are added.

These solutions remain stable (+/-10% degradation) for approximately 24 months, which is unheard of.

Figure 2:
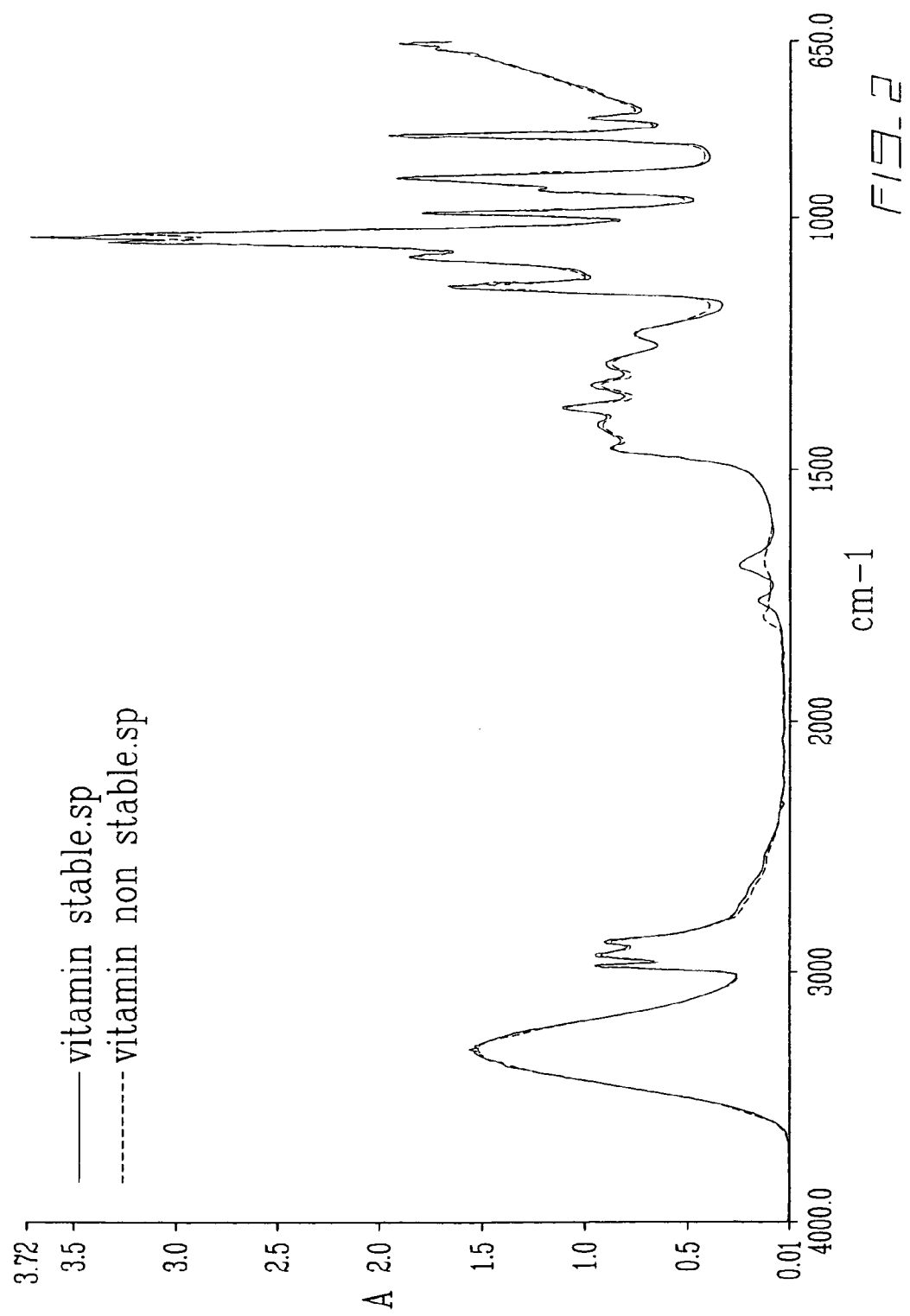
FIG. 2 represents comparative chromatograms of the solution of the present invention and a solution of vitamin C submitted to a controlled degradation.

FIG. 1 shows the location of the peaks of pure vitamin C. FIG. 2 shows that the maintenance of the peaks confirm that no significant degradation has occurred during the first 24 months of storage. A peak that would appear consequently to degradation is not observed in the chromatogram of the present solution.

The pH (dilution of 100 mL in water) for all 3 solutions ranges between 2.8 and 3.1.

The medium to high stirring of each ingredient added may be responsible to help form tiny water and vitamin-C spheres by "micronization" in the ethoxydiglycol/propylene glycol (both glycols) solution and because of the micronization occurring, it helps to reduce access of air which would inevitably oxidize the vitamin in the solution. It is also possible that a complex be formed between ascorbic acid and ethoxydiglycol.

EXAMPLE 7

Uses and Compositions

Therefore, the above solutions comprising a vitamin C that keeps all its integrity are intended to be used as is or through the making of a composition or a medication, to prevent or to treat any disease or disorder that involves or is caused by ROS or involving collagen synthesis. The disease or disorder includes but is not limited to skin cancer (melanoma), skin irritation or inflammation, dermatitis, skin allergy, psoriasis, acne, eczema, rosacea, radiations exposure including U.V. or sun exposure, depigmentation (skin whitening) and skin ageing (reduction of wrinkles inter alia). Compositions may comprise any suitable carrier which may include structuring agents (oils, fatty acids, surfactants, etc.) and a reducing agent or an anti-oxidant which would increase the stability of the ascorbic acid or which would complement its anti-oxidant properties. Further, compositions comprising any active ingredient which would benefit or not from the protective effect provided by vitamin C against oxidation are within the scope of the invention.

In adjunction with the present vitamin C, hydroquinone and kinetin have been used in examples provided herein to produce stabilized vitamin C compositions. The following currently used cosmetic or dermatologic products can all also be formulated in "combined" compositions: α-hydroxy acid, retinol, kojic acid, vitamin K, ascorbyl palmitate, magnesium ascorbyl phosphate and sodium ascorbyl phosphate. The combinations may include more than one of these products. The combination should remain at an acidic pH (below 7.0), and ideally below the pKa of ascorbic acid, when this pH(4.17) is compatible with the stability of the other products.

Although the present invention has been described hereinabove by way of preferred embodiments thereof, it can be modified, without departing from the spirit and nature of the subject invention as defined in the appended claims.

What is claimed is:

1. A stable solution which comprises more than zero and up to 15% L-ascorbic acid in a carrier comprising 10 to 15% water, 46.8 to 54.7% ethoxydiglycol, 22 to 29% propylene glycol, all percentages given by weight of final composition, the balance to 100% comprising a percentage of at least one anti-oxidant agent, said solution having a pH below 7.0.

2. The solution as defined in claim 1, wherein the at least one anti-oxidant agent comprises an anti-oxidant plant extract.

3. The solution as defined in claim 2, wherein the anti-oxidant plant extract is a grapefruit plant extract.

4. The solution as defined in claim 3, further comprising an additional anti-oxidant selected from the group consisting of kinetin and hydroquinone.

5. The solution as defined in claim 1, further comprising a fragrance material, with the following composition:

| water | 10%; |
|---|---|
| L-ascorbic acid | 5%; |
| ethoxydiglycol | 54.7%; |
| propylene glycol | 29%; |
| anti-oxidant plant extract | 1% and |
| fragrance material | 0.3%, | wherein all percentages are given by weight of final composition.

6. The solution as defined in claim 1, further comprising a fragrance material, with the following composition:

| water | 10%; |
|---|---|
| L-ascorbic acid | 10%; |
| ethoxydiglycol | 51.7%; |
| propylene glycol | 27%; |
| anti-oxidant extract | 1%; and |
| fragrance material | 0.3%, | wherein all percentages are given by weight of final composition.

7. The solution as defined in claim 1, further comprising a fragrance material, with the following composition:

| | |
|---|---|
| water | 15%; |
| L-ascorbic acid | 15%; |
| ethoxydiglycol | 46.8%; |
| propylene glycol | 22%; |
| anti-oxidant plant extract | 0.9%; and |
| fragrance material | 0.3%, | wherein all percentages are given by weight of final composition.

8. The solution as defined in claim 1, further comprising a fragrance material, and hydroquinone with the following composition:

| | |
|---|---|
| water | 12%; |
| L-ascorbic acid | 10%; |
| ethoxydiglycol | 48.90%; |
| propylene glycol | 26%; |
| anti-oxidant plant extract | 1%; |
| fragrance material | 0.1%; and |
| hydroquinone | 2%, | wherein all percentages are given by weight of final composition.

9. The solution as defined in claim 1, further comprising a fragrance material and hydroquinone, with the following composition:

| | |
|---|---|
| water | 12%; |
| L-ascorbic acid | 10%; |
| ethoxydiglycol | 46.90%; |
| propylene glycol | 26%; |
| anti-oxidant plant extract | 1%; |
| fragrance material | 0.1%; and |
| hydroquinone | 4%, | wherein all percentages are given by weight of final composition.

10. The solution as defined in claim 1, further comprising a fragrance material and kinetin, with the following composition:

| | |
|---|---|
| water | 10%; |
| L-ascorbic acid | 10%; |
| ethoxydiglycol | 51.88%; |
| propylene glycol | 27%; |
| anti-oxidant plant extract | 1%; |
| fragrance material | 0.1%; and |
| kinetin | 0.03%, | wherein all percentages are given by weight of final composition.

11. The solution as defined in claim 1 further comprising a topically suitable carrier or compound.

12. The solution as defined in claim 2 further comprising a topically suitable carrier or compound.

13. The solution as defined in claim 3 further comprising a topically suitable carrier or compound.

14. The solution as defined in claim 4 further comprising a topically suitable carrier or compound.

15. A topical composition comprising the solution as defined in claim 5, and a topically suitable carrier or compound, said composition having a pH below 7.0.

16. A topical composition comprising the solution as defined in claim 6, and a topically suitable carrier or compound, said composition having a pH below 7.0.

17. A topical composition comprising the solution as defined in claim 7, and a topically suitable carrier or compound, said composition having a pH below 7.0.

18. A topical composition comprising the solution as defined in claim 8, and a topically suitable carrier or compound, said composition having a pH below 7.0.

19. A topical composition comprising the solution as defined in claim 9, and a topically suitable carrier or compound, said composition having a pH below 7.0.

20. A topical composition comprising the solution as defined in claim 10, and a topically suitable carrier or compound, said composition having a pH below 7.0.

21. The solution as defined in claim 11 wherein said topically suitable carrier or compound is selected from the group consisting of tocopherol, tocopheryl acetate, retinol, retinyl palmitate, hydroquinone, proanthocyanidins, butylated hydroxytoluene, butylated hydroxyanisole, astaxanthin, alpha lipoic acid, tocotrienols, coenzyme Q10, α-hydroxy acid, kojic acid, kinetin, wine extract, vitamin K, ascorbyl palmitate, magnesium ascorbyl phosphate, sodium ascorbyl phosphate, a sun blocking agent and any combination thereof.

22. The solution as defined in claim 12 wherein said topically suitable carrier or compound is selected from the group consisting of tocopherol, tocopheryl acetate, retinol, retinyl palmitate, hydroquinone, proanthocyanidins, butylated hydroxytoluene, butylated hydroxyanisole, astaxanthin, alpha lipoic acid, tocotrienols, coenzyme Q10, α-hydroxy acid, kojic acid, wine extract, kinetin, vitamin K, ascorbyl palmitate, magnesium ascorbyl phosphate, sodium ascorbyl phosphate, a sun blocking agent and any combination thereof.

23. The solution as defined in claim 13 wherein said topically suitable carrier or compound is selected from the group consisting of tocopherol, tocopheryl acetate, retinol, retinyl palmitate, hydroquinone, proanthocyanidins, butylated hydroxytoluene, butylated hydroxyanisole, astaxanthin, alpha lipoic acid, tocotrienols, coenzyme Q10, α-hydroxy acid, kojic acid, wine extract, kinetin, vitamin K, ascorbyl palmitate, magnesium ascorbyl phosphate, sodium ascorbyl phosphate, a sun blocking agent and any combination thereof.

24. The solution as defined in claim 14 wherein said topically suitable carrier or compound is selected from the group consisting of tocopherol, tocopheryl acetate, retinol, retinyl palmitate, hydroquinone, proanthocyanidins, butylated hydroxytoluene, butylated hydroxyanisole, astaxanthin, alpha lipoic acid, tocotrienols, coenzyme Q10, α-hydroxy acid, kojic acid, wine extract, kinetin, vitamin K, ascorbyl palmitate, magnesium ascorbyl phosphate, sodium ascorbyl phosphate, a sun blocking agent and any combination thereof.

25. The topical composition as defined in claim 15 wherein said topically suitable carrier or compound is selected from the group consisting of tocopherol, tocopheryl acetate, retinal, retinyl palmitate, hydroquinone, proanthocyanidins, butylated hydroxytoluene, butylated hydroxyanisole, astaxanthin, alpha lipoic acid, tocotrienols, coenzyme Q10, α-hydroxy acid, kojic acid, wine extract, kinetin, vitamin K, ascorbyl palmitate, magnesium ascorbyl phosphate, sodium ascorbyl phosphate, a sun blocking agent and any combination thereof.

26. The topical composition as defined in claim 16 wherein said topically suitable carrier or compound is selected from the group consisting of tocopherol, tocopheryl acetate, retinol, retinyl palmitate, hydroquinone, proanthocyanidins, butylated hydroxytoluene, butylated hydroxyanisole, astaxanthin, alpha lipoic acid, tocotrienols, coenzyme Q10, α-hydroxy acid, kojic acid, wine extract, kinetin, vitamin K, ascorbyl palmitate, magnesium ascorbyl phosphate, sodium ascorbyl phosphate, a sun blocking agent and any combination thereof.

27. The topical composition as defined in claim 17 wherein said topically suitable carrier or compound is selected from the group consisting of tocopherol, tocopheryl acetate, retinol, retinyl palmitate, proanthocyanidins, butylated hydroxytoluene, butylated hydroxyanisole, astaxanthin, alpha lipoic acid, tocotrienols, coenzyme Q10, α-hydroxy acid, kojic acid, wine extract, kinetin, vitamin K, ascorbyl palmitate, magnesium ascorbyl phosphate, sodium ascorbyl phosphate, a sun blocking agent and any combination thereof.

28. The topical composition as defined in claim 18 wherein said topically suitable carrier or compound is selected from the group consisting of tocopherol, tocopheryl acetate, retinol, retinyl palmitate, proanthocyanidins, butylated hydroxytoluene, butylated hydroxyanisole, astaxanthin, alpha lipoic acid, tocotrienols, coenzyme Q10, α-hydroxy acid, kojic acid, wine extract, kinetin, vitamin K, ascorbyl palmitate, magnesium ascorbyl phosphate, sodium ascorbyl phosphate, a sun blocking agent and any combination thereof.

29. The topical composition as defined in claim 19 wherein said topically suitable carrier or compound is selected from the group consisting of tocopherol, tocopheryl acetate, retinol, retinyl palmitate, hydroquinone, proanthocyanidins, butylated hydroxytoluene, butylated hydroxyanisole, astaxanthin, alpha lipoic acid, tocotrienols, coenzyme Q10, α-hydroxy acid, kojic acid, wine extract, vitamin K, ascorbyl palmitate, magnesium ascorbyl phosphate, sodium ascorbyl phosphate, a sun blocking agent and any combination thereof.

30. The topical composition as defined in claim 20 wherein said topically suitable carrier or compound is selected from the group consisting of tocopherol, tocopheryl acetate, retinol, retinyl palmitate, hydroquinone, proanthocyanidins, butylated hydroxytoluene, butylated hydroxyanisole, astaxanthin, alpha lipoic acid, tocotrienols, coenzyme Q10, α-hydroxy acid, kojic acid, wine extract, vitamin K, ascorbyl palmitate, magnesium ascorbyl phosphate, sodium ascorbyl phosphate, a sun blocking agent and any combination thereof.

31. The solution of claim 1, said solution having a pH below 4.17.

* * * * *

UNITED STATES PATENT AND TRADEMARK OFFICE
CERTIFICATE OF CORRECTION

PATENT NO. : 7,342,045 B2  
APPLICATION NO. : 10/363929  
DATED : March 11, 2006  
INVENTOR(S) : Ghislain Vivier and Anthony Costa Page 1 of 1

It is certified that error appears in the above-identified patent and that said Letters Patent is hereby corrected as shown below:

Col. 10, Line 64, Claim 25 "retinal" should be -- retinol --

Signed and Sealed this

Nineteenth Day of August, 2008

JON W. DUDAS  
*Director of the United States Patent and Trademark Office*